(12) United States Patent
Jensen et al.

(10) Patent No.: US 8,864,723 B2
(45) Date of Patent: Oct. 21, 2014

(54) MALLEABLE TIP FOR AGENT APPLICATOR TO A TARGET SITE

(75) Inventors: Flemming Reissig Jensen, Hareskov (DK); Bettina Metzler, Charlottenlund (DK); Martin Bue Bertelsen, Copenhagen Ø (DK); Rasmus Kaastrup Torekov, Copenhagen NV (DK)

(73) Assignee: Ferrosan Medical Devices A/S, Soeborg (DK)

( * ) Notice: Subject to any disclaimer, the term of this patent is extended or adjusted under 35 U.S.C. 154(b) by 0 days.

(21) Appl. No.: 13/502,578

(22) PCT Filed: Sep. 13, 2010

(86) PCT No.: PCT/EP2010/005598
§ 371 (c)(1),
(2), (4) Date: Apr. 18, 2012

(87) PCT Pub. No.: WO2011/047753
PCT Pub. Date: Apr. 28, 2011

(65) Prior Publication Data
US 2012/0209216 A1    Aug. 16, 2012

(51) Int. Cl.
*A61M 5/00* (2006.01)
*A61M 35/00* (2006.01)

(52) U.S. Cl.
CPC .................................. *A61M 35/003* (2013.01)
USPC ......................................................... 604/239

(58) Field of Classification Search
USPC .............. 604/82, 191, 264, 528, 103.03, 239, 604/311, 523, 274
See application file for complete search history.

(56) References Cited

U.S. PATENT DOCUMENTS 5,540,464 A    7/1996  Picha
2006/0253082 A1   11/2006  McIntosh et al.

OTHER PUBLICATIONS

Office Action dated Mar. 1, 2012 from U.S. Appl. No. 12/581,458.

*Primary Examiner* — Nicholas Lucchesi
*Assistant Examiner* — Brooke Matney
(74) *Attorney, Agent, or Firm* — K. David Crockett, Esq.; Crockett & Crockett, PC (57) ABSTRACT

An applicator device for applying an agent to a target site with a malleable tip that can be cut to length with a pair of nursing dressing scissors or similar type of scissors and a malleable tip with a formable tube that that can be cut to length with a pair of nursing dressing scissors or similar type of scissors. The malleable tip is configured for passage of fluid therethrough and includes a malleable member. The malleable member is made of a soft metal that is strong enough to retain the shape of the tip after is has been bend into configuration, but soft and weak enough to be easily cut with a pair of nursing dressing scissors or the like. A method for preparing an applicator device that is suitable for applying an agent to a target site during or before an operation, comprising providing an applicator device with a formable tip, forming said tip to a desired configuration and cutting said formable tip to a desired length with a pair of nursing dressing scissors or similar type of scissors.

21 Claims, 12 Drawing Sheets

MALLEABLE TIP FOR AGENT APPLICATOR TO A TARGET SITE

FIELD

The present disclosure generally relates to devices and systems for applying medical fluids to a target site. More particularly, the present disclosure relates to surgical or hemostatic applicators that include a malleable section, which can be bent and retained in a desired configuration.

BACKGROUND

SURGIFLO® by Ferrosan™ is a pre-filled surgical hemostatic applicator that includes a pre-filled, flowable hemostat in a syringe that offers the option to customize the consistency by controlling the amount of saline or thrombin used. The flowable hemostat is a haemostatic Matrix, which is a sterile, absorbable porcine gelatin or other anti-bleeding agent. An applicator tip is secured to the syringe via a Luer-lock. The flowable haemostatic agent product is applied to a target area by positioning the free end of the applicator tip near a target site and then expelling an amount of the flowable haemostat. The surgical or haemostatic applicator is supplied with two applicator tips for precise placement of the flowable. This gives surgeons an option of choosing between a flexible and malleable applicator tip that has "memory" to ensure it stays at the optimum angle for easier access and exact product placement, and a non-malleable tip that can be cut with nursing dressing scissors to a desired length for providing the required penetration depth.

The SURGIFLO® surgical or haemostatic applicator is particularly useful in connection with minimally invasive surgical techniques wherein a plurality of devices may be introduced into the body through small incisions. One example of a common minimally invasive surgery involves laparoscopic surgical procedures. Laparoscopic procedures may be used to treat hernias, colon dysfunctions, gastroesophageal reflux disease, and gallbladder disorders. These procedures are considered minimally invasive, and typically a patient undergoing one of the procedures returns home hours after undergoing surgery.

Generally, laparoscopic procedures require making at least one small incision in the patient's body near the area of interest. A cannula or trocar may be inserted into the incision for convenient instrument access. Thereafter, various surgical instruments are introduced into the patient's body through the incision(s). Generally, these instruments enable the surgeon to visualize the inside of the patient's body and access the internal organs of the patient. Current laparoscopic surgical instruments include cameras, scissors, dissectors, graspers and retractors. One of the difficulties presented when performing minimally invasive surgical procedures relates to applying a hemostat to a target area. Applying the hemostat to the bleeding site may be difficult as the site may be some distance within the body and access is limited. Moreover other parts of the body may impede the manipulation of an elongated catheter to reach these relatively remote sites. This problem can be reduced by using the known formable or malleable tip.

The known malleable tip retains the desired configuration until it is reshaped into a different configuration and it is shaped or formed, typically by manual bending, into a desired configuration.

The known malleable/formable tip includes a tube with a large lumen configured to receive the flowable from the syringe. A malleable insert in the form of a steel wire is positioned within a second smaller lumen of the malleable tip. The malleable insert assists in retaining the formable tip in the desired configuration.

The ability to shape the formable section increases the ability to accurately position the applicator device, while minimizing the user's manipulation of the device.

SUMMARY

On this background, the inventors have arrived at the insight that it would be advantageous to provide a tip that is malleable and can be cut to a desired length with a pair of nurses dressing scissors. Such a tip could be shaped and trimmed by a surgeon, nurse or other medical staff in situ so that the surgeon has a tip available with the desired shape and length as the actual situation on the operation table requires.

However, steel wire that is sturdy enough to provide the required assistance in retaining the formable tip in the desired configuration cannot be cut with nursing dressing scissors.

In one embodiment an applicator device for applying a flowable agent to a target site is provided. The applicator device includes a tip with a proximate end for securing to an agent delivery apparatus and a free distal end. The tip is malleable or formable. The tip can be cut to length with a common pair of nursing dressing scissors. The ability to shape the tip to the desired configuration and the ability to trim the tip to the desired length increase the ability to accurately position the applicator device, while minimizing the user's manipulation of the device.

In another embodiment an applicator device for applying an agent to a target site is provided. The applicator device, includes a formable tip configured for the passage of fluid therethrough, the formable tip having a proximal end portion and a distal end portion, the proximal end portion configured for communication with at least one fluid reservoir, the formable tip configured to be shaped into a desired configuration and the formable tip is configured to be cut to a desired length with a common pair of nurses dressing scissors.

In another embodiment a tip for applying an agent to a target site is provided. The tip includes a formable tube configured for the passage of fluid therethrough, said formable tube being configured to be able to be trimmed to length by cutting the formable tube with a pair of nursing dressing scissors or similar type of scissors.

In another embodiment a method for preparing an applicator device that is suitable for applying an agent to a target site before or during an operation is provided. The method includes providing an applicator device with a formable tip, forming said tip to a desired configuration and cutting said formable tip to a desired length with a pair of nursing dressing scissors or similar type of scissors.

It is accordingly an advantage of the present disclosure to provide a medical fluid application tip that can be cut to length with nursing dressing scissors and can bent by applying manual force to a position and maintain that position during application of the medical fluid.

It is another advantage of the present disclosure to provide a medical fluid application tube or tip that can cut to length in situ with dressing scissors and that can be bent into an application position when needed.

It is another advantage of the present disclosure to provide a medical fluid application tube or tip that can cut to length in situ with dressing scissors and that can be bent into an application position when needed with little or no risk of the tip collapsing when it is bend.

It is a further advantage of the present disclosure to provide a medical fluid application tube or tip that can trimmed by a user and that can be bent to an application position and maintain itself in that position until changed.

Additional features and advantages are described herein, and will be apparent from, the following Detailed Description and the figures.

BRIEF DESCRIPTION OF THE DRAWINGS

In the following detailed portion of the present description, the teachings of the present document will be explained in more detail with reference to the exemplary embodiments shown in the drawings, in which:

FIG. 9b is an isolated view of another embodiment of a piece of a malleable member used in the tip shown in FIGS. 1 to 8.

DETAILED DESCRIPTION

In the following detailed description, the applicator device according to this disclosure will be described by the exemplary embodiments.

Figure 1:
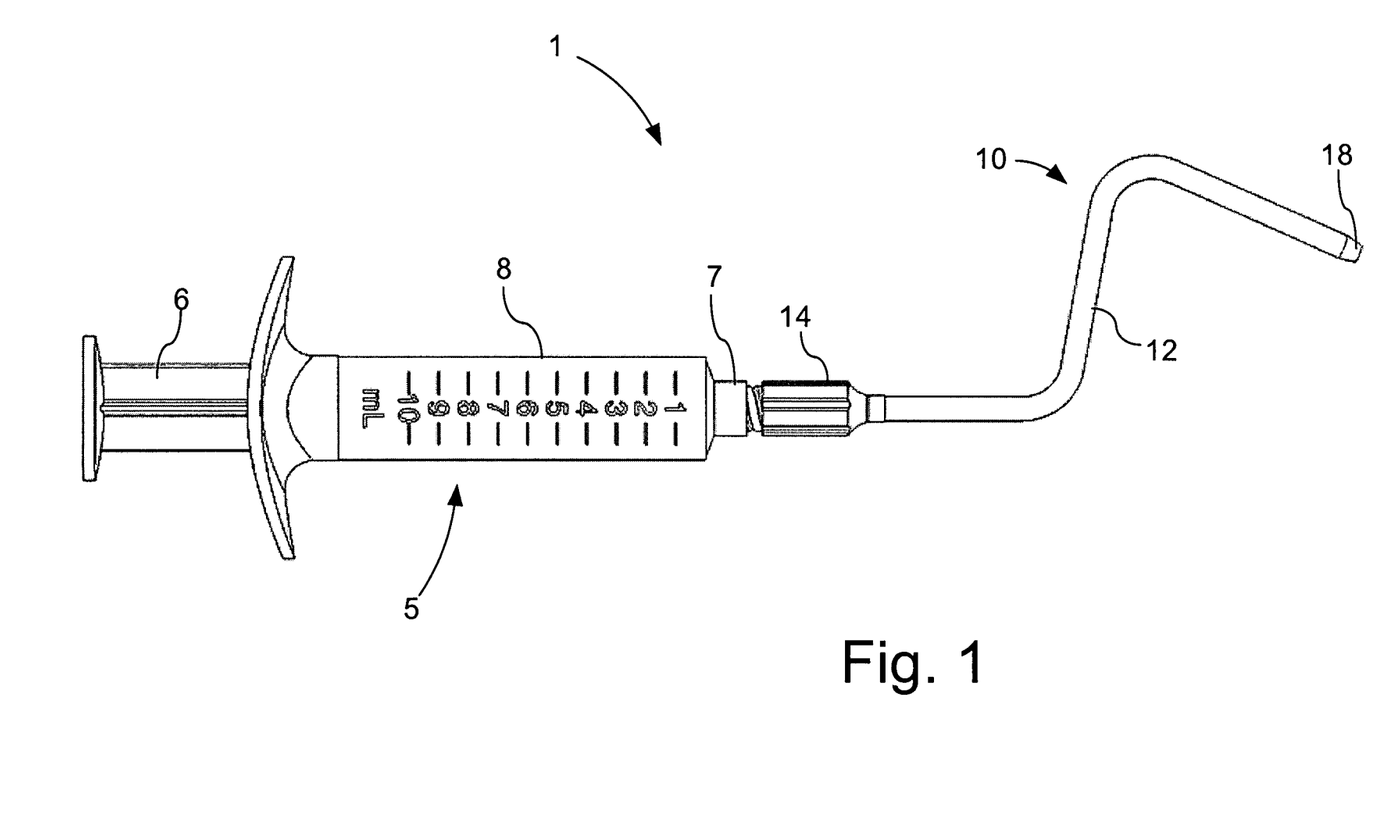
FIG. 1 is a view of one embodiment of surgical or hemostatic application system.

Referring now to the drawings and in particular to FIG. 1, system 1 generally illustrates one exemplary embodiment of a system for applying an agents, such as a haemostatic or a tissue sealant, to a target site within a body. The haemostat can be, for example, a bioresorbable gelatin matrix with or without thrombin.

One suitable haemostat can be SURGIFLO® haemostatic Matrix manufactured by the assignee of the present disclosure.

The applicator device is connected to a manually operated syringe material applicator 5. The syringe material applicator 5 is provided with a male Luer lock connector 7 and comprises a plunger 6 and a reservoir 8 containing the agent or medical fluid.

The material applicator 5 supplies an agent or medical fluid to the applicator device. It should be understood that the embodiment of material applicator 5 is shown by way of example and not limitation. Additionally, the material applicator may employ alternative structures, such as multiple reservoirs.

In general the applicator device includes a tip or delivery shaft 10. The tip 10 includes a tube 12 with a proximate end and a distal end 18. A Luer anchor 14 is secured to the proximate end. The distal end 18 is the free end of the tip 10.

In one embodiment, the tip 10 is inserted through a small surgical incision to position the free end 18 at or adjacent to a target site. When free end 18 is in the desired position, the haemostatic can be transmitted from material applicator 5, through tube 12, and applied to the target site the free end 18. In the shown embodiment the free end of the tip 18 is provided with a conical distal portion. This conical portion 18 is not essential and the extremity of the tip 10 may just as well be formed by the tube 12 without the conical portion.

As can be seen in FIG. 1, the tube 12 can be formed or shaped into a desired shape or configuration by applying force, typically by hand, to bend the formable section. Tube 12 retains the configuration until force is again applied to the tube to form the tube into a different configuration. In the example shown, formable tube 12 is bent at about somewhat less than ninety-degree angle and a somewhat more than ninety-degree angle. It should be understood that formable tube 12 could be bent at a variety of angles, including multiple angles, and shaped into a variety of custom configurations depending on the particular procedure or location of the target site. The bending and shape retention of formable tube 12 is discussed in more detail below.

Figure 2:
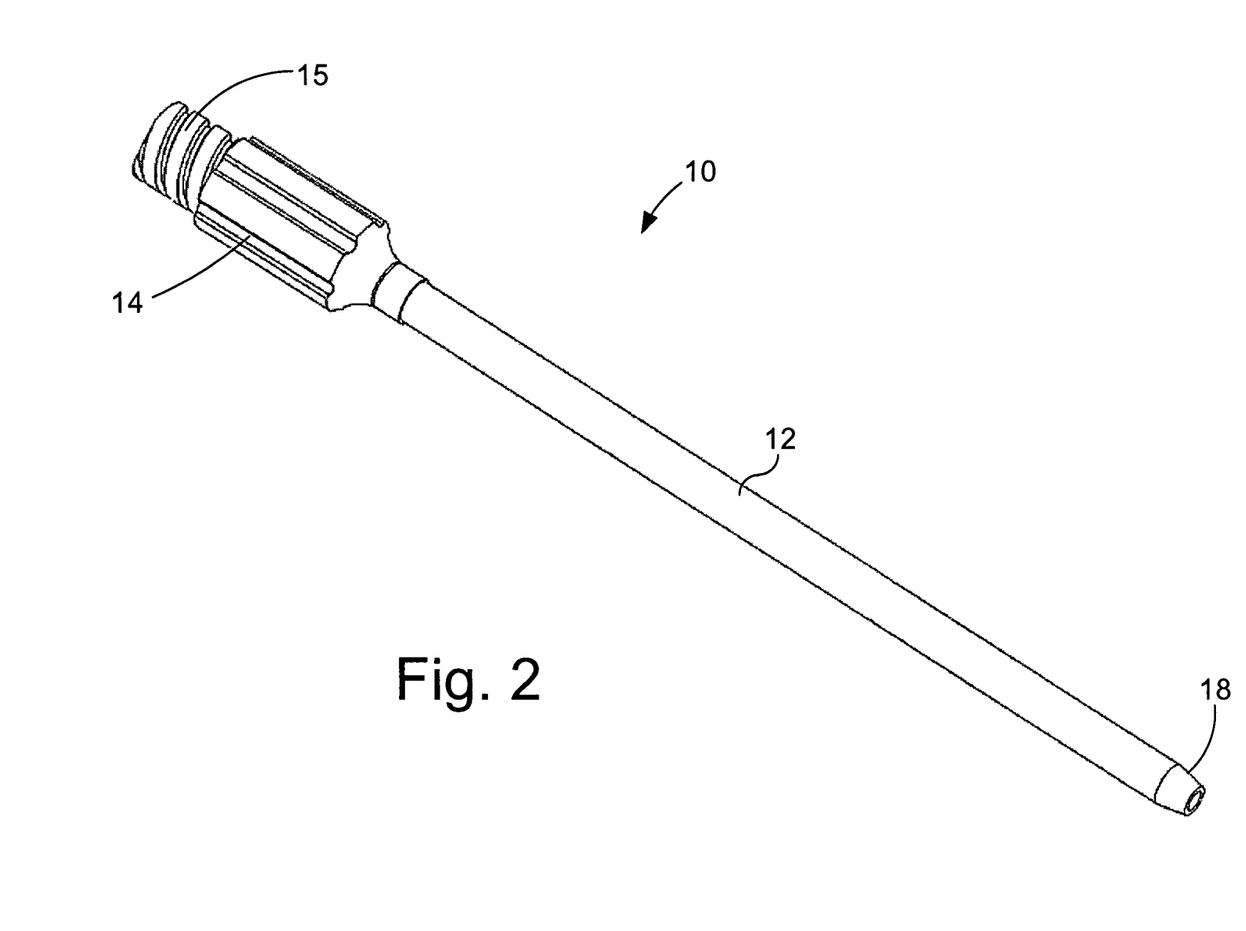
FIG. 2 is an elevated view of the tube or tip shown in FIG. 1 in a straight configuration.

FIG. 2 shows the tip 10 in a straight configuration, and not connected to another device, i.e. the configuration it will typically have when it is packaged. In an embodiment, the applicator tip 10 is part of a kit that comprises at least one material applicator 5, such as a syringe and one or more formable applicator tips 10 in a sterile package, such as a blister pack (not shown).

In a surgical environment there are typically a variety of types of scissors available for cutting patient tissue and one type of scissor for cutting dressing and other items that need to be cut to shape or length. The latter are so called dressing scissors or nursing dressing scissors also called Mayo scissors and these scissors are not used on the patient. Hereafter the term "nursing dressing scissors" will be used but it should be noted that this term equally covers scissors that are denoted as "Mayo scissors". Dressing scissors are relatively standardized around the world and the standard are stainless steel scissors with a length of approximately 12.5 cm to approximately 17.5 cm (approximately 5 to approximately 7 Inches).

The formable tip according to the present embodiment can be cut with a pair of standard dressing scissors by applying a force to the scissors that is within the comfortable range for an average operator like a nurse or surgeon, i.e. less than 80 Nm.

Tests with a pair of 17 cm long nursing dressing scissors on the formable tip 10 according to the present embodiment showed that the force that needs to be applied to the handles/finger holes 32 to cut the tube 12 was between 30 N and 60 N.

Figure 3:
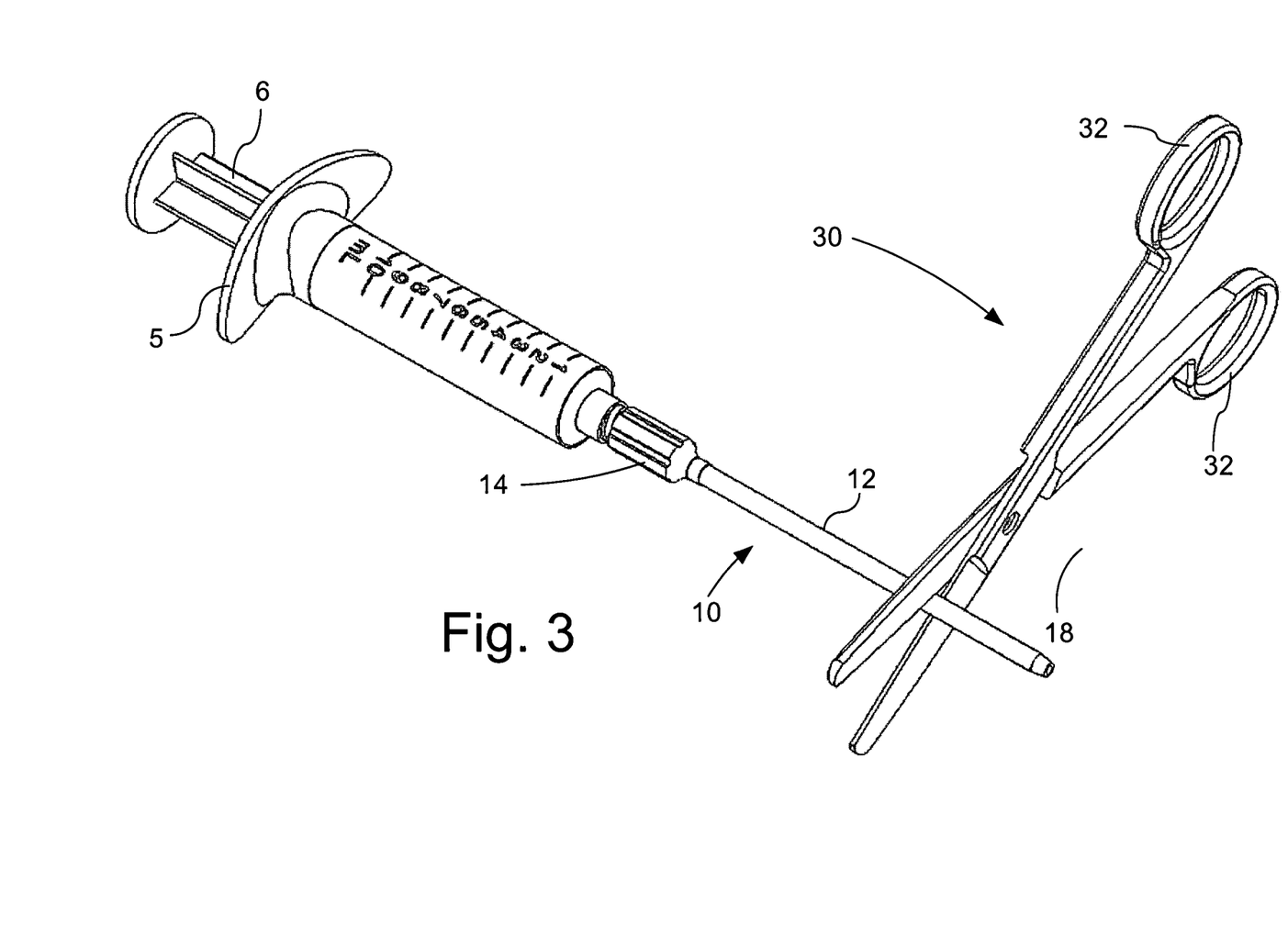
FIG. 3 is an elevated view of the straight tip connected to a material applicator with the a pair of scissors being in place to cut the tip to length.

FIG. 3 shows the applicator tip 10 connected via the Luer-lock to the material applicator 5 and in the same straight configuration as in FIG. 2. A pair of nursing dressing scissors 30 has been brought in position for cutting the tip 10 to a desired length. The scissors 30 may be operated by a surgeon, a nurse or other medical staff on the operation floor. The tip 10 has been configured so that it can be cut with a common pair of nursing dressing scissors 30 by applying a force to the handles/fingerholes 32 that is within the comfort zone of an average operator of the scissors.

Figure 4:
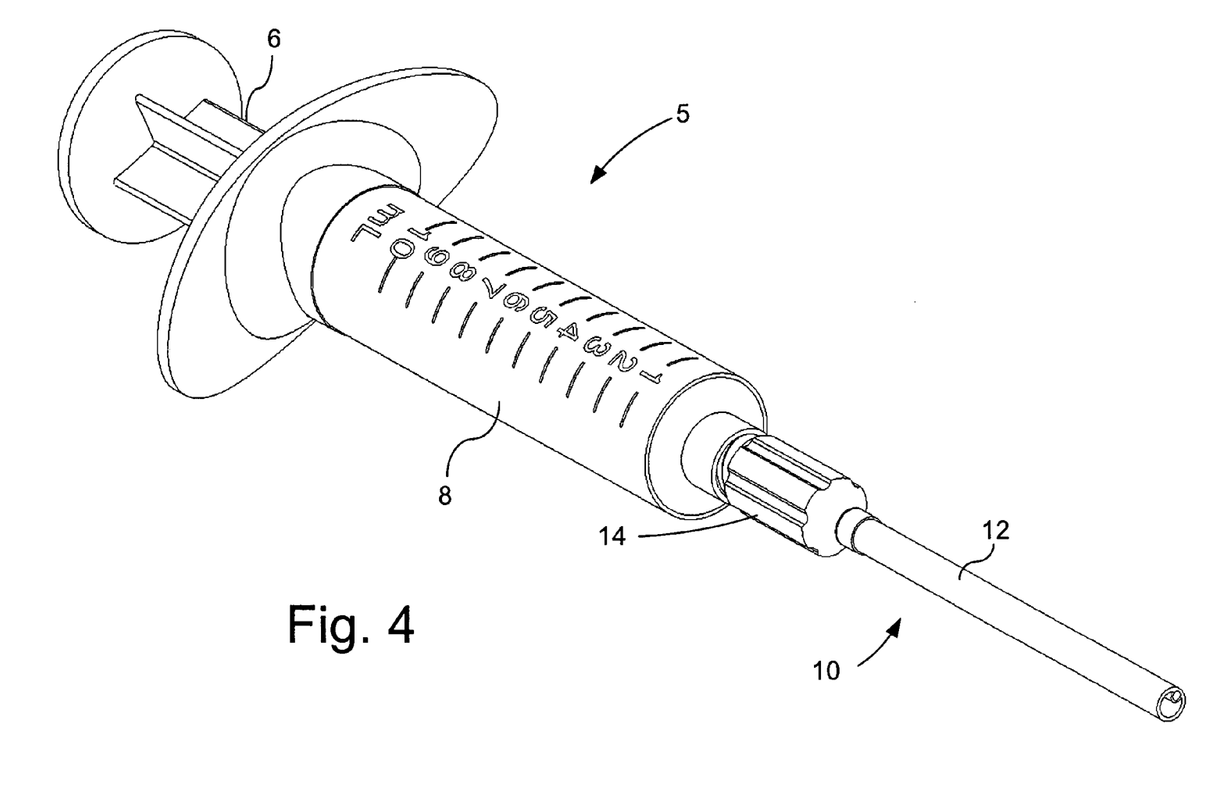
FIG. 4 shows the tip of FIG. 3 after it has been cut to length.

FIG. 4 shows the applicator tip 10 of FIG. 3 after it has been cut to a desired length.

Figure 5:
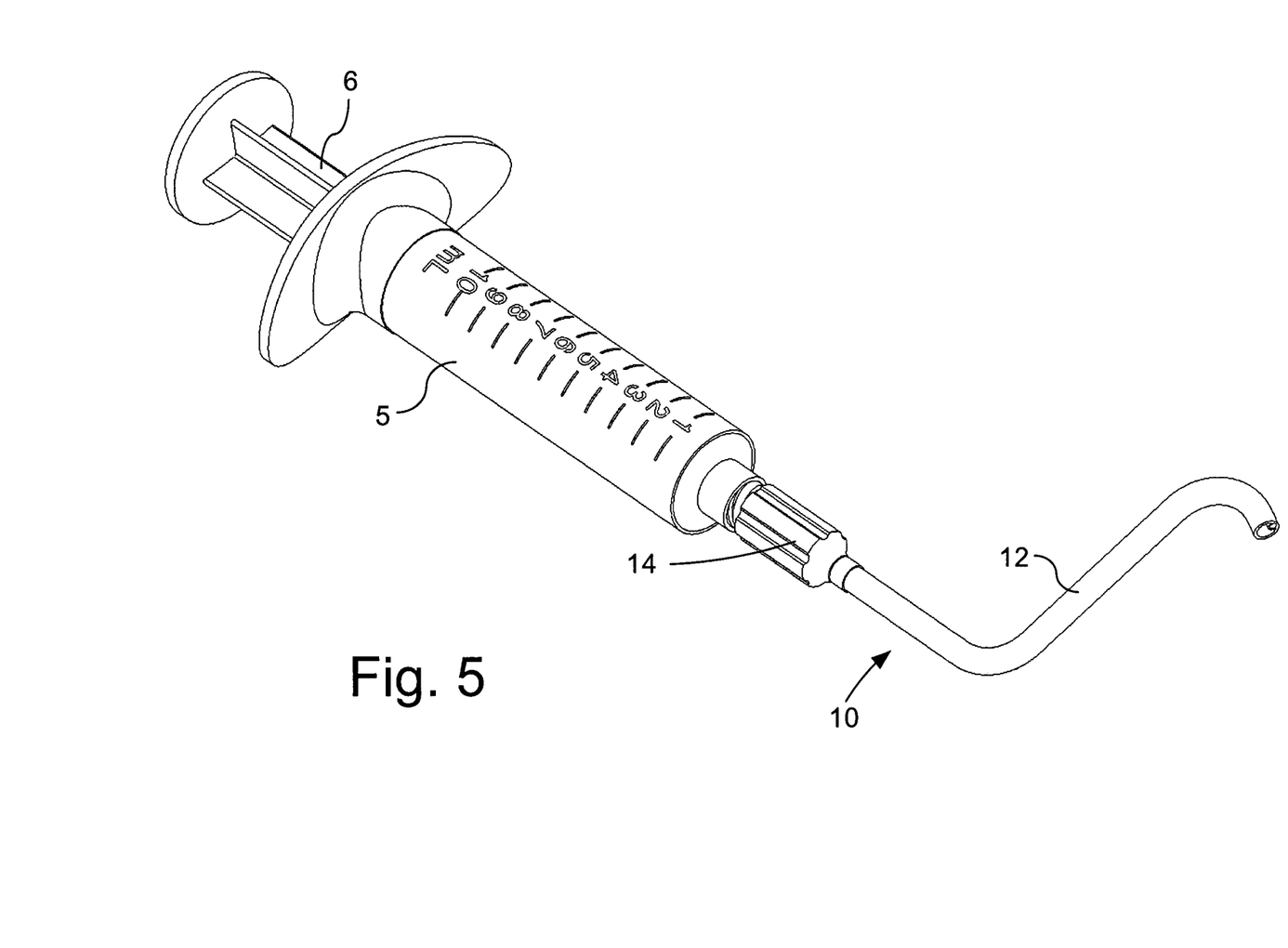
FIG. 5 shows the tip of FIG. 4 after is has been bend into shape.

FIG. 5 shows the applicator tip 10 of FIG. 4 after it has been bent into a desired shape.

Figure 6:
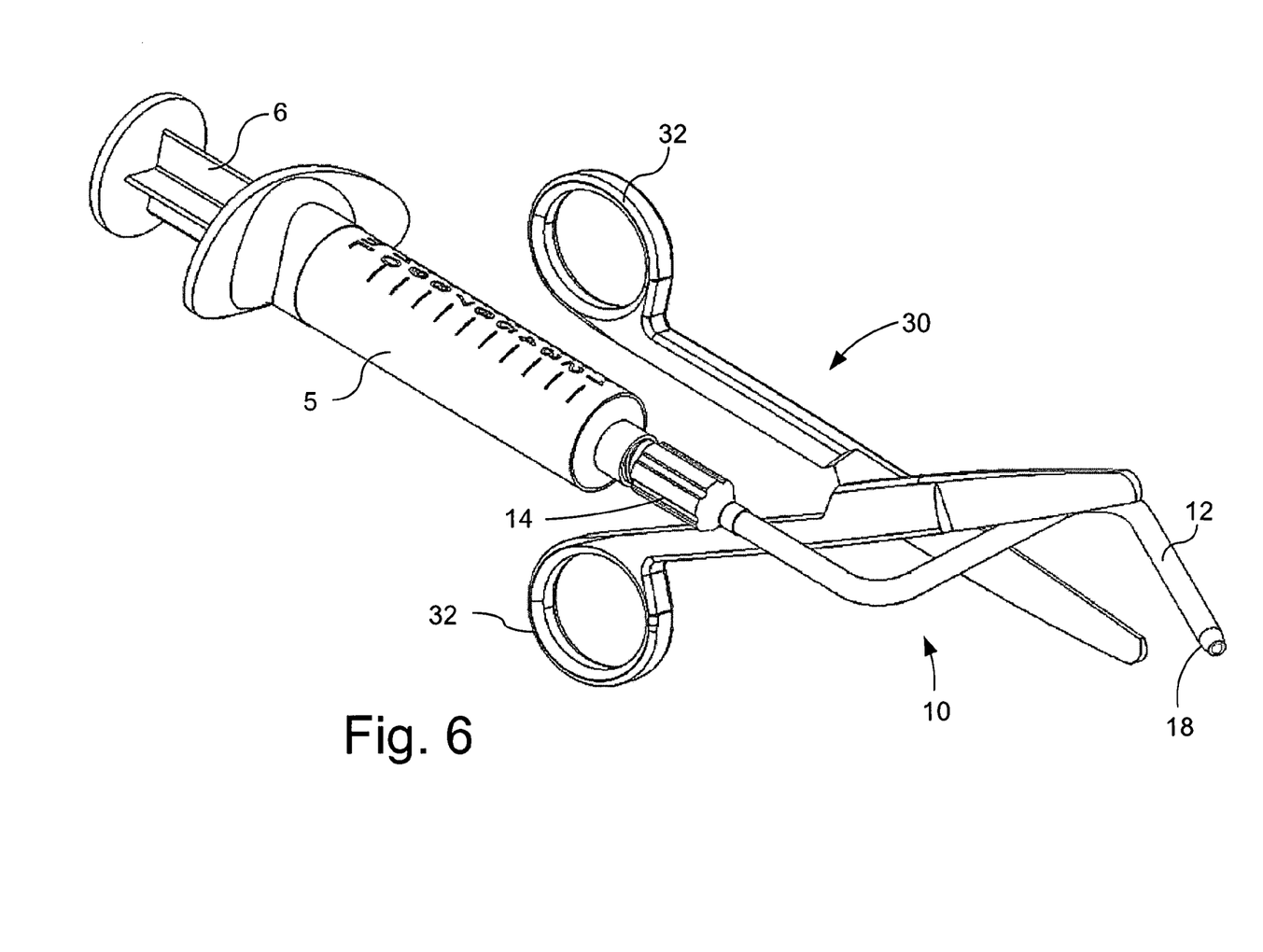
FIG. 6 is an elevated view of the anticoagulant application system of FIG. 1 and a pair of nursing dressing scissors, where the tip or tube is about to be cut to length with the nursing dressing scissors.

FIG. 6 shows the applicator tip 10 connected via the Luer-lock to the material applicator 5 and in the same double bent configuration as in FIG. 1. A pair of nursing dressing scissors 30 has been brought in position for cutting the tip 10 to a desired length. The scissors 30 may be operated by a surgeon, a nurse or other medical staff on the operation floor. The tip 10 has been configured so that it can be cut with a common pair of nursing dressing scissors 30 by applying a force to the handles/fingerholes 32 that is within the comfort zone of an average operator of the scissors.

According to an exemplary embodiment, the procedure according to the present disclosure involves preparing the applicator device before its actual deployment. A material applicator 5 is filled with a suitable agent (which could be a haemostatic matrix) with an applicator tip 10 connected to the material applicator 5. Next, the surgeon or other medical staff shapes the tip 10 in a desired configuration and determines the desired length. If the desired length is less than the actual length the surgeon or other medical staff, uses a pair of nursing dressing scissors 30 to cut the tip 10 to a desired length. Alternatively, another regular pair of scissors similar to nursing dressing scissors may be used to cut the applicator tip 10. Preferably, the cut is made at an angle of approximately ninety degrees to the (local) axial extend of the tube to avoid the creation of an angled and sharp free end of the tip 10. This concludes the preparation of the applicator device 1.

Thereafter, the actual deployment of the applicator device 1 commences, for example by a surgeon placing the free end of the tip 10 in proximity of a target site and the agent is applied by manually pressing the plunger 6 of the material applicator 5.

If, after cutting, the tip 10 is still longer than desired it can be cut again in accordance with the procedure above.

Figure 7:
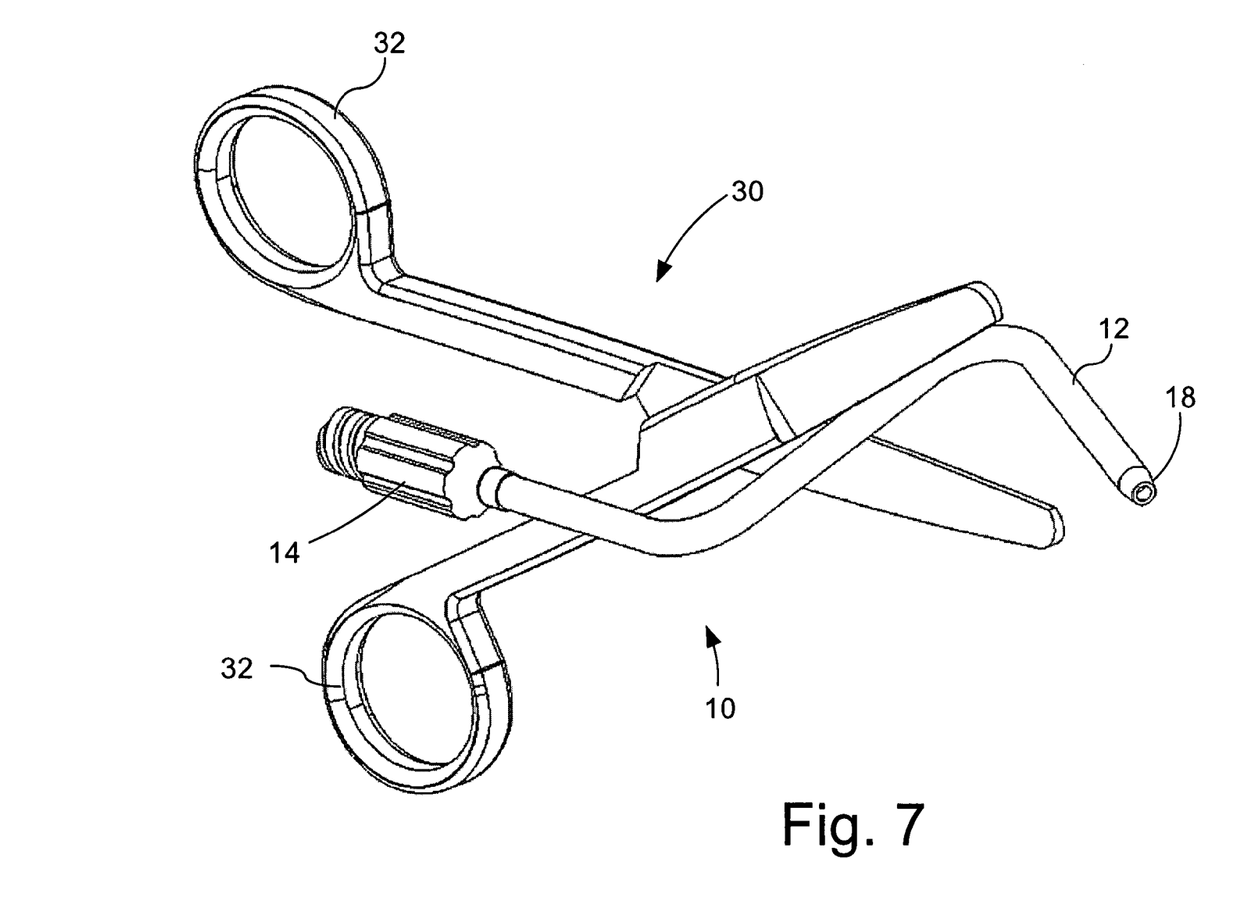
FIG. 7 is an elevated view of the tube or tip shown in FIG. 1 and a pair of nursing dressing scissors, where the tip or tube is about to be cut to length with the nursing dressing scissors.

According to an embodiment shown in FIG. 7, the applicator tip 10 is cut whilst it is not connected to the material applicator 5. In this embodiment the applicator tip 10 can be cut to desired length before it is attached to the material applicator 5. After the applicator tip 10 is cut, it is attached to the material applicator 5 and the agent is applied to the target area as described above.

The tip 10 can be cut to length before bending it to shape or after bending it into shape.

With reference to FIGS. 8 to 11 the construction of the formable applicator tip 10 including the features allowing it to malleable or formable as well as being able to be cut with a pair of nursing dressing scissors 30 or similar scissors is explained in detail.

The tube 12 is made of a suitable plastic or polymer material. The polymer or plastic material should have to a certain extend one or more of the following properties: easy to deform and stretch, stable enough to provide the tube with resistance to collapsing, elongation at breaking larger than 10%, low modulus of elasticity, good adhesive properties especially at low temperatures, low melt flow viscosity, kink resistance, stable material properties after sterilization with radiation.

The following is a non-exhaustive list of suitable materials for the tube material: Polyolefin, polyethylene, polypropylene, polyether with rigid polyamide, PVC, acryl nitrile butadiene styrene (ABS), Polytetrafluoro-ethylene (PTFE). Mixtures of these materials are also suitable. Preferably, the plastic material is relatively soft and preferably the hardness of the plastic material is in the range of 60 to 95, preferably approximately 85 Type A Shore Durometer.

In an embodiment the plastic (polymer) material for the tube 12 is a medical grade polymer material. In another embodiment the plastic (polymer) material for the tube 12 is an extrusion grade and in yet another embodiment the plastic (polymer) material for the tube is a medical grade and extrusion grade polymer, preferably a thermoplastic polyolefin based polymer.

Preferably, the tube material should be suitable for being used in an injection molding or extrusion process.

Figure 8:
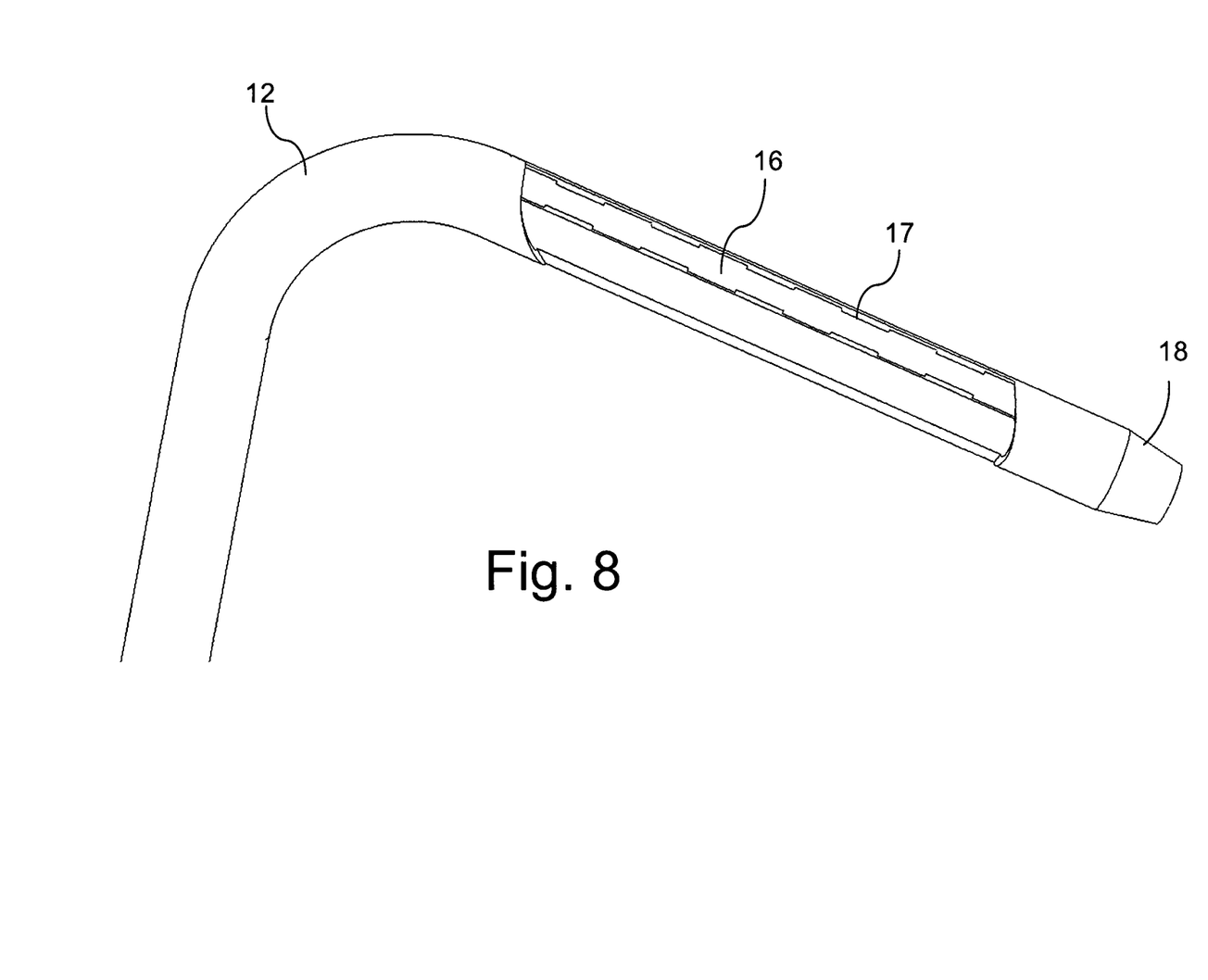
FIG. 8 is a detailed and partially cut open view of the tube or tip shown in FIG. 1.
Figure 10:
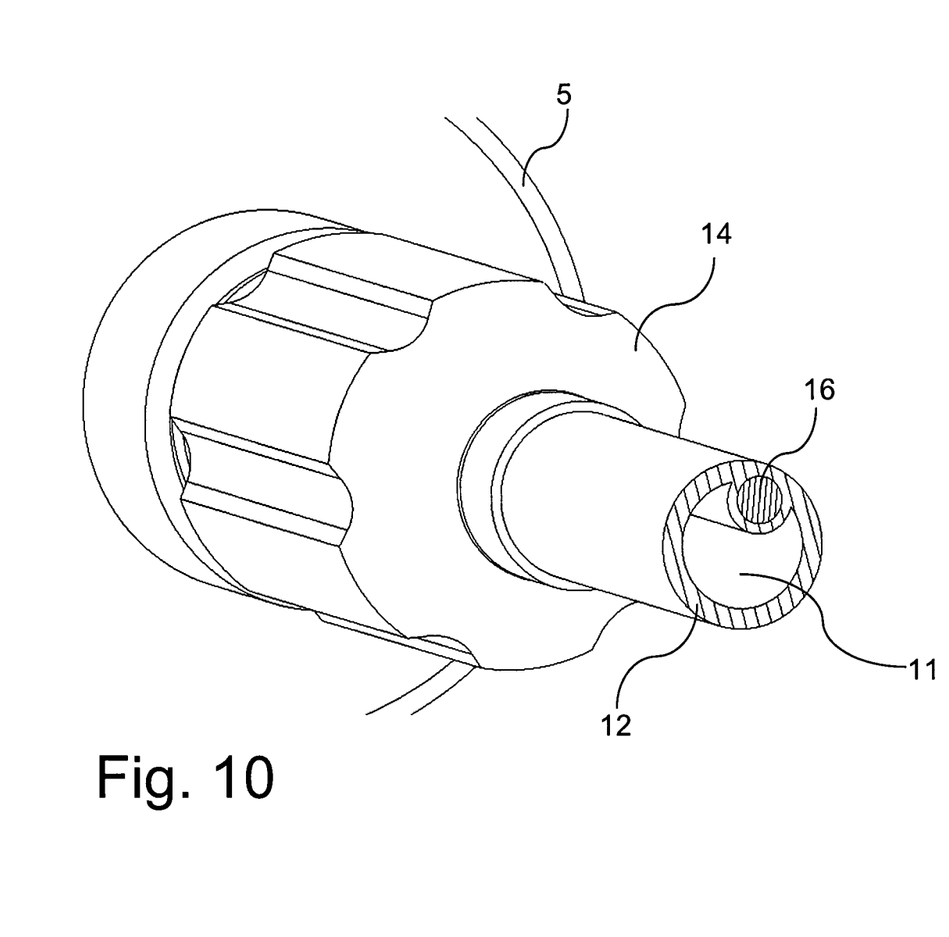
FIG. 10 is a cross-sectional view through of the tube or tip shown in FIG. 1.
Figure 11:
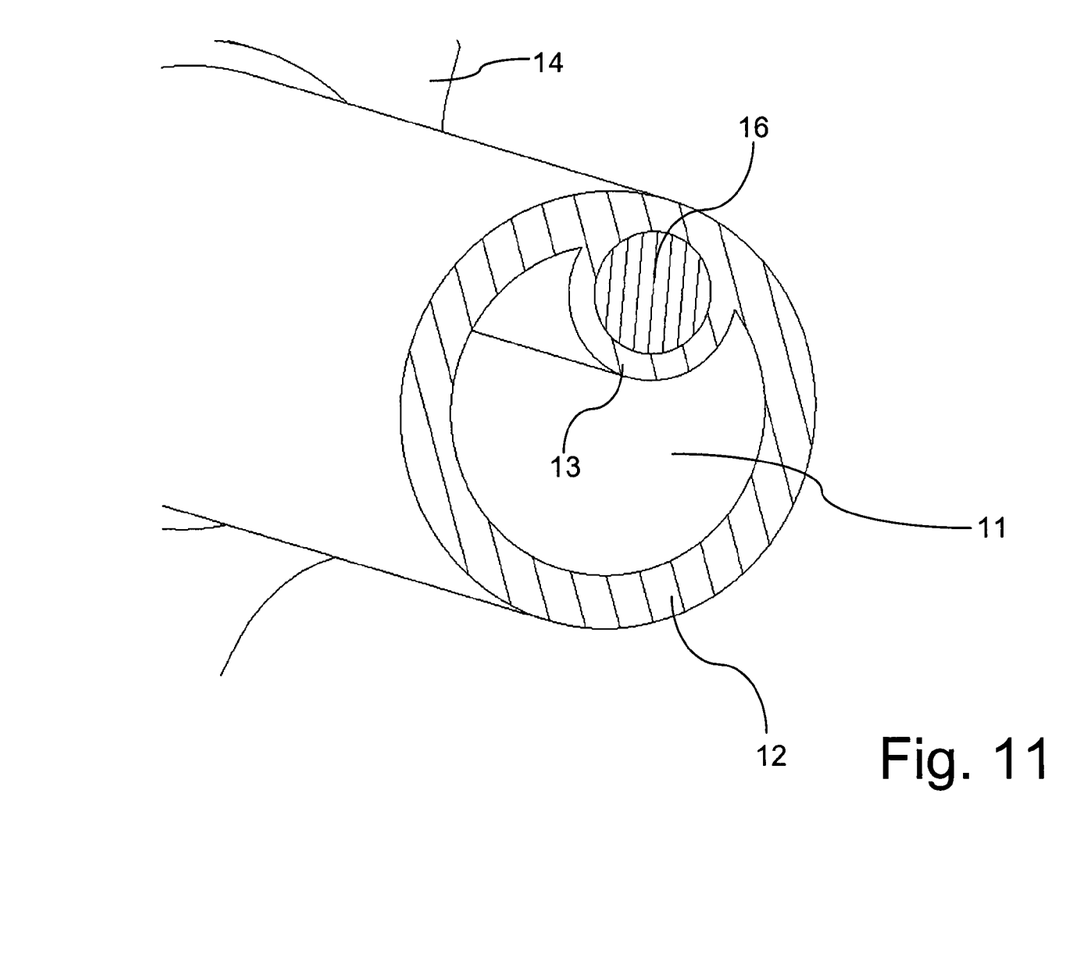
FIG. 11 is a detailed cross-sectional view through of the tube or tip shown in FIG. 1.

The tube 12 has a large lumen 11 for transport of the agent and a smaller lumen in which a malleable member 16 is received. In the present exemplary embodiment the tube 12 has a circular cross-sectional outline. However, the tube 12 may have another cross-sectional outline, such as oval, hexagonal, pentagonal or other polygon shape.

The malleable member 16 is made of a soft metal or other suitable material that is strong enough to maintain the desired configuration after bending, but at the same time soft and weak enough to be cut with regular nursing dressing scissors 30 or the like. Relatively pure aluminum (approximately 99.00 to 99.99%) has been found to be a suitable material. However, aluminum alloys and other soft metals such as zinc, tin, gold, silver, titanium, copper, lead or alloys thereof and biocompatible plastics such as PEEK (polyether ether ketone) and HDPE (high density polyethylene are also examples of suitable materials.

Suitable materials for the malleable member have: a hardness ranging from Brinell 10HB to 50HB, a Young's modulus ranging from 50 GPa to 120 GPa and a shear modulus of 10 GPa to 50 GPa.

Preferably, the aluminium is medical grade aluminium or food grade aluminium. An example of a suitable aluminium grade is according to product specification 99.9% pure aluminium EN AW-1090.

The malleable member 16 extends the full length of the tube 12. The malleable member 16 does not extend into the distal end 18.

In the present exemplary embodiment the malleable member is an aluminum wire with a circular cross-sectional shape and a diameter of approximately 1.3 mm. A suitable diameter for the malleable member 16, depending on the properties of the metal or alloy used for a tip with a single malleable member is approximately 0.8 to 2.0 mm.

The cross-section of the malleable member 16 can have other shapes, such as oval, square, or other polygonal shape.

The diameter of the tube 12 can vary between approximately 2.5 mm and approximately 7.0 mm, preferably approximately 4 mm. The wall thickness of the tube 12 is between 0.25 and 0.65 mm, preferably approximately 0.4 mm. The combination of the choice of the plastic or polymer material and the dimensions of the tube allows for a construction in which the risk of the tube collapsing when bend is minimized.

The malleable member 16 is provided with a surface that improves adhesion with the plastic or polymer material of the tube 12.

In one embodiment, shown in FIG. 9b, the wire of the malleable member 16 for the malleable member is an extruded aluminum wire and the outer surface of the wire is a smooth surface as obtained by an the extrusion process and thoroughly cleaned after the extrusion process to ensure that there are no residues of the lubrication oil used for the extrusion process on the outer surface.

Figures 9, 9A:
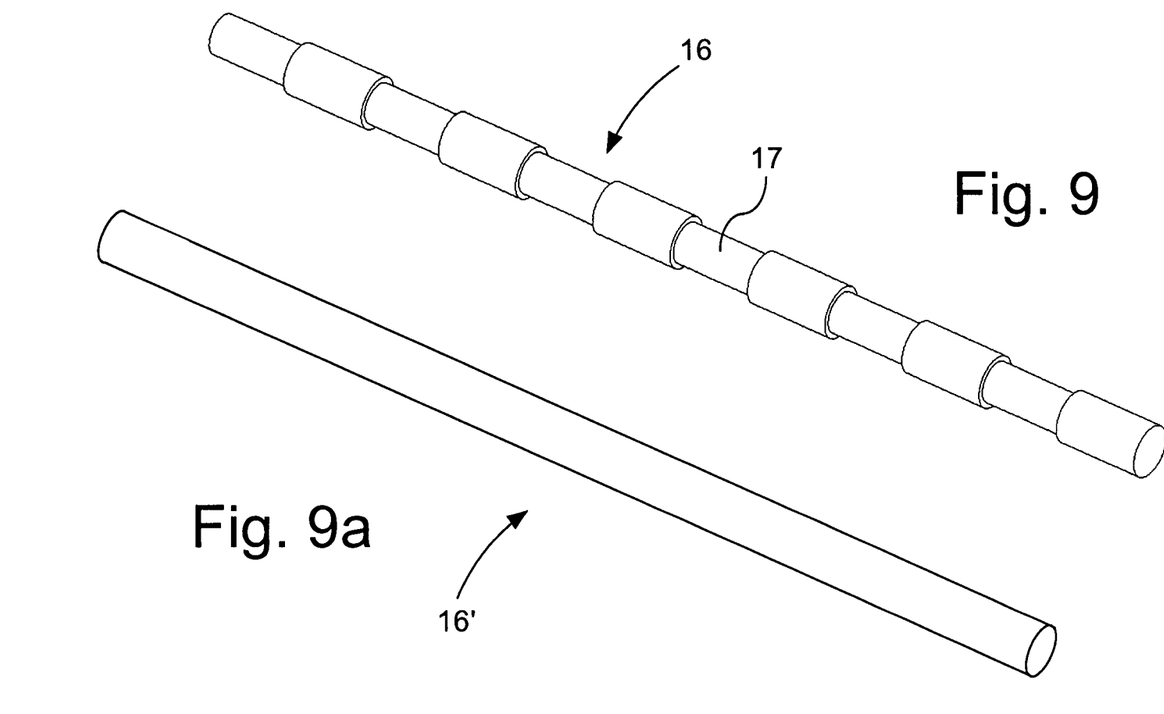
FIG. 9a is an isolated view on a piece of a malleable member used in the tip shown in FIGS. 1 to 8.

In another embodiment shown in FIG. 9a the surface of the wire of the malleable member 16 is provided with serrations or grooves 17 in the surface. The serrations 17 can be substantially circumferentially directed grooves around the wire 16, but can also have another direction or be other shape or pattern. In an embodiment the tube material is molded around the malleable member 16 and the tube material thereby fills the serrations and envelops the malleable member 16 and creates strong bonding and/or engagement of the malleable ember 16 and the tube material. As illustrated in FIG. 9a, the grooves extend continuously around the outer surface of the malleable member to form complete grooves in a plane perpendicular to a longitudinal axis of the malleable member.

When the tube 12 is bent the wire may 16 tend to get displaced in a longitudinal direction relative to the tube material.

Displacement between the malleable member 16 and the tube material could result in the wire material of the malleable member 16 protruding from the tube material after the tip 10 has been cut with the scissors 30. A protruding portion of wire is undesirable since the wire end could be sharp and cause damages to patient tissue. By securing good adhesion between the tube material and the malleable member 16 protrusion of a portion of the malleable member from the tube material is prevented since the tube material is forced to stay with the malleable member 16.

Surface roughness and/or serrations or other deviations from a smooth surface can be used to improve the adhesion between the tube material and the malleable member 16.

The adhesion between the tube material and the malleable member 16 ensures a smooth surface at the free end of the formable tip 10 after a cut with the scissors 30.

In an embodiment the malleable member 16 and the tube 12 are produced in an extrusion process. The pre-produced wire for the malleable member 12 is fed to an extrusion machine with that has an extrusion mold and heated to approximately 180-230 Deg. Celsius at position where the wire is introduced into the extrusion process that forms the tube 12 with the wire integrated therein. The plastic material for the tube is also heated before and during the extrusion process to 80-120 Deg. Celsius.

The elevated temperature of both the wire and the plastic material ensures a good adhesion between the wire and the plastic material, for wire with a smooth surface, for wire with a rough surface and for wire with serrations or grooves. Thus, when the extruded tubing 12 with the embedded wire therein is cools down to ambient temperature there is a good bond between the outer surface of the wire and the tube material and the tube material adheres to the wire surface. This good bond prevents the tube from collapsing when the tube is bend and prevents that a portion of the malleable member material protrudes from the tubing material after the tube has been cut with a pair of scissors.

In an embodiment the Luer anchor 14 is made from the same plastic or polymer material as the tube 12.

FIG. 10 shows the free end of the tip 10 after being cut to length.

Figure 12:
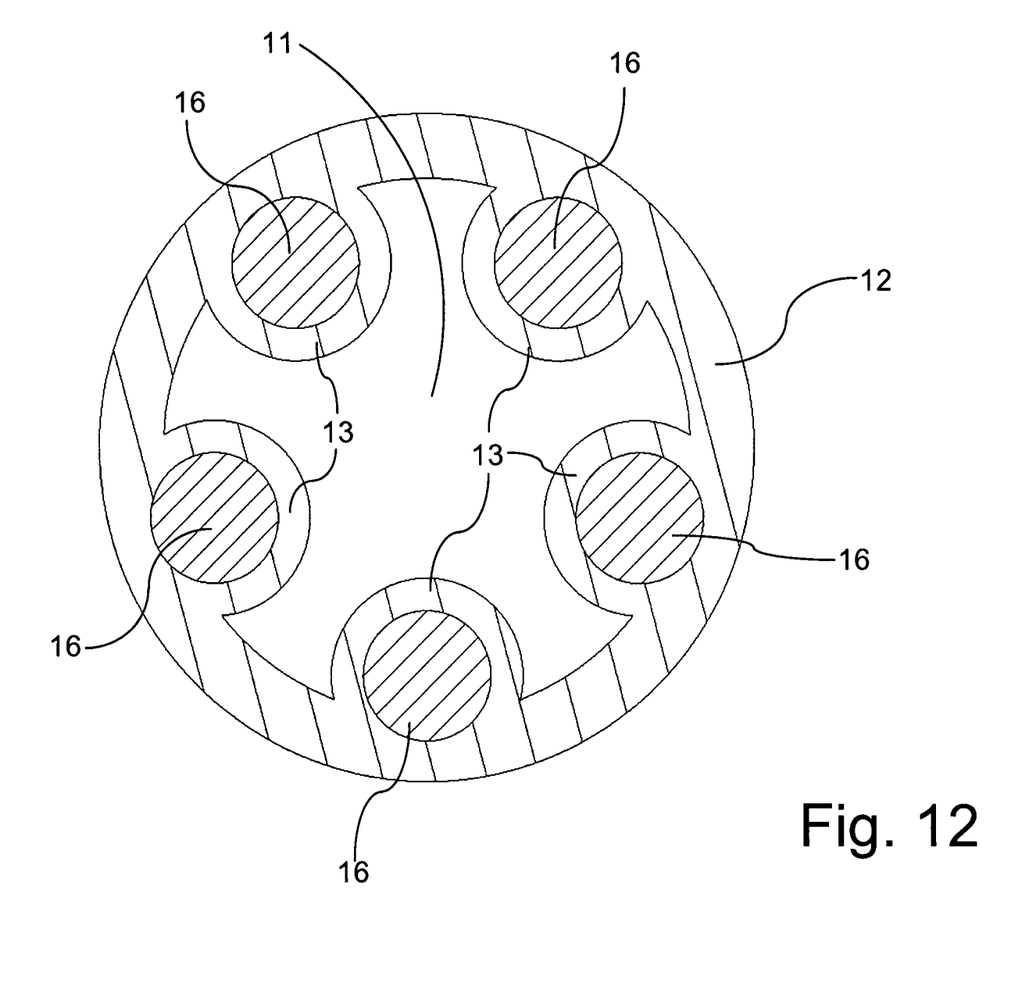
FIG. 12 is a cross-sectional view through another exemplary embodiment of the tip or tube.

FIG. 12 shows another embodiment of the malleable or formable tube 12 in a cross-sectional view. The tube 12 according to this embodiment can be used with the applicator device described above. In an elevated view the tube according to this embodiment looks like the tube 12 in FIG. 2.

The tube 12 is made of a plastic or polymer material with the same properties and materials as the tube according to the embodiment above.

The tube 12 has a large lumen 11 for transport of the agent and five smaller lumens in each of which a malleable member 16 is received. In the present exemplary embodiment the tube has a circular cross-sectional outline. However, the tube 12 may have another cross-sectional outline, such as oval, hexagonal, pentagonal or other polygon shape.

The malleable members 16 are made of the same type of metal as the malleable member 16 in the embodiment above, i.e. a soft metal that is strong enough to maintain the desired configuration after bending, but at the same time soft and weak enough to be cut with regular nursing dressing scissors 30 or similar scissors.

In the present exemplary embodiment the malleable members are aluminum wires with a circular cross-sectional shape and a diameter of 0.8 mm but may vary from approximately 0.4 mm to approximately 1.0 mm.

The cross-section of the malleable members can have other shapes, such as oval, square or polygonal.

The malleable members 16 are provided with a surface that improves adhesion with the plastic or polymer material of the tube 12. In one embodiment the surface is provided with grooves or serrations 17. The serrations 17 can be substantially circumferentially directed grooves on the wires 16, but can also be other shape of serrations. The tube material is molded around the wires and will envelop the wire and the serrations completely for optimal adhesion between the two materials.

When the tube 12 is bend the wires 16 may tend to get displaced in a longitudinal direction relative to the tube material.

Displacement between the malleable members 16 and the tube material could result in one or more of the wires 16 protruding from the tube material after the tip has been cut with the scissors 30. A protruding portion of wire is undesirable since the wire end could be sharp and cause damages to patient tissue. By securing good adhesion between the tube material and the malleable members 16 protrusion of a portion of the malleable members 16 from the tube material is prevented.

Surface roughness and/or serrations or other deviations from a smooth surface can be used to improve the adhesion between the tube material and the malleable members 16.

The adhesion between the tube material and the malleable members 16 ensures a smooth surface at the free end of the formable tip 10 after a cut with the scissors 30.

According to other embodiments (not shown) the malleable member or members in the formable tube 12 can be arranged in other configurations than parallel with the longitudinal extension of the tube 12. The malleable member or members could for example be arranged in spiral configurations or as a mesh. The mesh can consist of a plurality of parallel wires and annular rings.

Further, the formable tip has been shown with a single lumen for fluid transport. However, a formable tip with a plurality of lumens for fluid transport, which formable tip can be cut to length with a normal pair of nursing dressing scissors is also part of this disclosure.

Although the malleable member has been descried as a solid member it is also possible to have a compound structure with different materials or identical materials such as a bundle of fine fibers or rods of any of the materials mentioned hereabove or combinations of these materials. Alternatively, the malleable member can be made form multiple rigid pieces contained inside an elastomeric construct. The bending moment applied to the malleable section will result in restacking of the rigid pieces to a new state that is at a particular angle. The elastomeric construct will contribute to the rigidity of the system.

The nursing dressing scissors shown in this disclosure have a blunt tip on both blades. It is noted that nursing dressing scissors with sharp tips and with one sharp tip and one blunt tip may equally be used. The expression "can be cut with a pair of scissors" in this application is to indicate that the cut can be made without extreme effort of an operator and/or and without substantially damaging the scissors.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. An applicator device for applying an agent to a target site, comprising:
a formable tip configured for the passage of fluid therethrough, the formable tip having a proximal end portion and a distal end portion, the proximal end portion configured for communication with at least one fluid reservoir, the formable tip configured to be shaped into a desired configuration and to be cut to a desired length with a common pair of nursing dressing scissors, wherein the formable tip comprises a formable or malleable tube with a lumen for transport of the agent and at least one lumen in which a malleable member is received,
wherein the malleable member is made of a soft metal that is strong enough to maintain the desired configuration after bending, but at the same time soft and weak enough to be cut with nursing dressing scissors or similar scissors;
wherein the surface of the malleable member is provided with serrations and the serrations are substantially circumferentially directed grooves, and said grooves extend continuously around the outer surface of the malleable member to form a complete groove in a plane perpendicular to a longitudinal axis of the malleable member.

2. An applicator device according to claim 1, wherein the malleable member has a circular cross-sectional shape and a diameter between approximately 0.8 and approximately 2.0 mm if there is one malleable member and the malleable members have a diameter between approximately 0.3 mm and 1.0 mm when the tip is provided with more than one malleable member.

3. An applicator device according to claim 1, wherein the formable tip can be cut with a pair of nursing dressing scissors or similar pair of scissors by applying a force to the handles or finger holes that does not exceed 80 Newton.

4. An applicator device according to claim 1, wherein the tube comprises a material which adheres to the surface of the malleable member.

5. An applicator device according to claim 1, wherein the malleable member has a hardness ranging from Brinell 10HB to 50HB, a Young's modulus ranging from 50 GPa to 120 GPa and a shear modulus of 10 GPa to 50 GPa.

6. The applicator device of claim 1 wherein said malleable member is a wire extending substantially in the direction of the longitudinal extension of the tube member.

7. The applicator device of claim 1 wherein said malleable member comprises a soft metal.

8. The applicator device of claim 1 wherein said malleable member comprises plastic.

9. The applicator device of claim 1 wherein said malleable member comprises an aluminum wire.

10. A tip for use with an applicator device for applying an agent to a target site, said tip comprising:
a formable tube configured for the passage of fluid therethrough, said formable tube being configured to be able to be trimmed to length by cutting the formable tube with a pair of nursing dressing scissors or similar type of scissors, wherein said formable or malleable tube with a lumen for fluid passage and at least one lumen wherein a malleable member is received,
wherein the malleable member is strong enough to maintain the desired configuration after bending, but at the same time soft and weak enough to be cut with nursing dressing scissors or similar scissors;
wherein the surface of the malleable member is provided with serrations and the serrations are substantially circumferentially directed grooves, and said grooves extend continuously around the outer surface of the malleable member to form a complete groove in a plane perpendicular to a longitudinal axis of the malleable member.

11. A tip according to claim 10, wherein the malleable member has a circular cross-sectional shape and a diameter between approximately 0.3 mm and approximately 2.0 mm.

12. A tip according to claim 10, wherein the tip can be cut with a pair of nursing dressing scissors or similar pair of scissors by applying a force to the handles or finger holes that does not exceed 80 Newton.

13. A tip according to claim 10, wherein the malleable member has a hardness ranging from Brinell 10HB to 50HB, a Young's modulus ranging from 50 GPa to 120 GPa and a shear modulus of 10 GPa to 50 GPa.

14. The applicator device of claim 10 wherein said malleable member is a wire extending substantially in the direction of the longitudinal extension of the tube member.

15. The applicator device of claim 10 wherein said malleable member comprises a soft metal.

16. The applicator device of claim 10 wherein said malleable member comprises plastic.

17. The applicator device of claim 10 wherein said malleable member comprises an aluminum wire.

18. An applicator device for applying an agent to a target site, comprising:
a formable tip configured for the passage of fluid therethrough, the formable tip having a proximal end portion and a distal end portion, the proximal end portion configured for communication with at least one fluid reservoir, the formable tip configured to be shaped into a desired configuration and to be cut to a desired length with a common pair of nursing dressing scissors, wherein the formable tip comprises a formable or malleable tube with a lumen for transport of the agent and at least one lumen in which a malleable member is received,
wherein the malleable member is made of a soft metal that is strong enough to maintain the desired configuration after bending, but at the same time soft and weak enough to be cut with nursing dressing scissors or similar scissors;
wherein the surface of the malleable member is provided with serrations and the serrations are substantially circumferentially directed grooves, and said grooves extend continuously around the outer surface of the malleable member to form a substantially complete groove in a plane substantially perpendicular to a longitudinal axis of the malleable member.

19. An applicator device according to claim 18, wherein the malleable member has a circular cross-sectional shape and a diameter between approximately 0.8 and approximately 2.0 mm if there is one malleable member and the malleable members have a diameter between approximately 0.3 mm and 1.0 mm when the tip is provided with more than one malleable member.

20. An applicator device according to claim 18, wherein the formable tip can be cut with a pair of nursing dressing scissors or similar pair of scissors by applying a force to the handles or finger holes that does not exceed 80 Newton.

21. An applicator device according to claim 18, wherein the tube comprises a material which adheres to the surface of the malleable member.

\* \* \* \* \*